United States Patent
Roth et al.

(10) Patent No.: US 9,284,416 B2
(45) Date of Patent: Mar. 15, 2016

(54) PROCESS FOR CONVERTING A SOLID (METH)ACRYLATE COPOLYMER INTO A DISPERSED FORM BY MEANS OF A DISPERSING AGENT

(75) Inventors: Erna Roth, Darmstadt (DE); Ruediger Alexowsky, Nauheim (DE); Hans-Ulrich Petereit, Darmstadt (DE); Kathrin Nollenberger, Frankfurt (DE); Christian Meier, Darmstadt (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 13/504,527

(22) PCT Filed: Nov. 16, 2009

(86) PCT No.: PCT/EP2009/065244
§ 371 (c)(1),
(2), (4) Date: Apr. 27, 2012

(87) PCT Pub. No.: WO2011/057676
PCT Pub. Date: May 19, 2011

(65) Prior Publication Data
US 2012/0208832 A1 Aug. 16, 2012

(51) Int. Cl.
| | |
|---|---|
| *A61K 47/32* | (2006.01) |
| *C08K 5/11* | (2006.01) |
| *C08K 5/1535* | (2006.01) |
| *A61P 11/00* | (2006.01) |
| *C08K 5/41* | (2006.01) |
| *C09D 105/00* | (2006.01) |
| *A61K 31/522* | (2006.01) |
| *C08L 5/00* | (2006.01) |
| *C08K 5/06* | (2006.01) |
| *C08J 3/03* | (2006.01) |
| *A61K 9/50* | (2006.01) |
| *C08J 3/05* | (2006.01) |
| *A61K 9/28* | (2006.01) |

(52) U.S. Cl.
CPC ............... *C08J 3/03* (2013.01); *A61K 9/5026* (2013.01); *A61K 9/5089* (2013.01); *C08J 3/05* (2013.01); *A61K 9/284* (2013.01); *C08J 2333/14* (2013.01)

(58) Field of Classification Search
CPC ............ C08J 2333/14; C08J 3/03; C08J 3/05
USPC ........... 514/263.34, 772.6; 524/57, 314, 310, 524/111, 277, 156
See application file for complete search history.

(56) References Cited

U.S. PATENT DOCUMENTS

| | | | | |
|---|---|---|---|---|
| 4,737,357 | A * | 4/1988 | Lehmann et al. | 424/487 |
| 5,587,149 | A * | 12/1996 | Punto et al. | 424/59 |
| 6,207,184 | B1 | 3/2001 | Ikeda et al. | |
| 6,348,532 | B1 | 2/2002 | Mayer | |
| 7,465,774 | B1 * | 12/2008 | Schade et al. | 526/318.3 |
| 2003/0206939 | A1 * | 11/2003 | Bannister | 424/440 |
| 2005/0142174 | A1 * | 6/2005 | Assmus et al. | 424/449 |
| 2012/0071565 | A1 | 3/2012 | Roth et al. | |

FOREIGN PATENT DOCUMENTS

| | | |
|---|---|---|
| CN | 1243851 A | 2/2000 |
| EP | 0 181 515 | 5/1986 |
| EP | 0 352 800 A2 | 1/1990 |
| EP | 0 965 626 | 12/1999 |
| JP | 2-73011 A | 3/1990 |
| JP | 2001-48990 A | 2/2001 |
| JP | 03/057199 A1 | 7/2003 |
| JP | 2005-506323 A | 3/2005 |
| JP | 2005-519054 A | 6/2005 |
| JP | 2006-45134 A | 2/2006 |
| WO | 02 09675 | 2/2002 |
| WO | 03/020241 A2 | 3/2003 |
| WO | 03 057199 | 7/2003 |

OTHER PUBLICATIONS

International Search Report Issued Jul. 29, 2010 in PCT/EP09/65244 Filed Nov. 16, 2009.
U.S. Appl. No. 13/378,112, filed Dec. 14, 2011, Roth, et al.
U.S. Appl. No. 13/376,529, filed Dec. 6, 2011, Roth, et al.
Office Action issued on Mar. 5, 2013 in the corresponding Chinese Patent Application No. 200980162478.1 (with English Translation).
Japanese Office Action dated Aug. 19, 2013, issued in corresponding Japanese patent application No. 2012-539188.

\* cited by examiner

*Primary Examiner* — Anna Falkowitz
(74) *Attorney, Agent, or Firm* — Oblon, McClelland, Maier & Neustadt, L.L.P.

(57) ABSTRACT

The present invention provides a process for converting a solid (meth)acrylate copolymer into a dispersed form by preparing an aqueous dispersion comprising the components (a) a (meth)acrylate copolymer which is composed of free-radical polymerized methyl methacrylate, ethylacrylate and a salt of 2-trimethylammoniumethyl methacrylate, present in solid form as a powder or as a granulate, (b) up to 50% by weight calculated on the (meth)acrylate copolymer (a) of a dispersing agent selected from the groups of (b) i) plasticizers in combination with emulsifiers and/or (b) ii) pharmaceutically acceptable carbohydrates having 6 to 18 carbon atoms with a functional group and (c) water by mixing the components (a), (b) and (c) to give a suspension which becomes an aqueous dispersion during the conversion of the solid (meth)acrylate copolymer into the dispersed form, characterized in that, the (meth)acrylate copolymer is converted into the dispersed form by means of the presence of the dispersing agent at a temperature of less than 50° C.

28 Claims, No Drawings

US 9,284,416 B2

PROCESS FOR CONVERTING A SOLID (METH)ACRYLATE COPOLYMER INTO A DISPERSED FORM BY MEANS OF A DISPERSING AGENT

CROSS REFERENCE TO RELATED APPLICATION

This application is a 35 U.S.C. §371 national stage patent application of international patent application PCT/EP09/065244, filed on Nov. 16, 2009, the text of which is incorporated by reference.

The present invention refers to a process for converting a solid (meth)acrylate copolymer into a dispersed form by means of a dispersing agent. The aqueous dispersion is containing a cationic (meth)acrylate copolymer and a dispersing agent for facilitating the step of dispersing. The step of dispersing can be carried out at a lower temperature.

TECHNICAL BACKGROUND

U.S. Pat. No. 4,737,357 describes a method for producing a film-forming aqueous dispersions and coating agent for pharmaceuticals comprising a (meth)acrylate copolymer which is composed of free-radical polymerized methyl methacrylate, ethylacrylate, and 2-trimethylammoniumethyl methacrylate chloride, wherein the step of dispersing is carried out at temperatures of 60 to 80° C.

EP-A 0 463 877 describes pharmaceutical compositions with delayed active ingredient release consisting of a core with an active pharmaceutical ingredient as a monolayer coating film which comprises a water-repellent salt and a water-insoluble copolymer of ethyl acrylate, methyl methacrylate and trimethylammoniumethyl methacrylate chloride. The water-repellent salt may be for example Ca stearate or Mg stearate. Sigmoidal release plots are obtained.

EP-A 0 436 370 describes pharmaceutical compositions with delayed active ingredient release consisting of a core with an active pharmaceutical ingredient and an organic acid and an outer coating film which has been applied by aqueous spraying and is a copolymer of ethyl acrylate, methyl methacrylate and trimethylammoniumethyl methacrylate chloride. In this case, sigmoidal release plots are likewise obtained.

WO 00/19984 describes a pharmaceutical preparation consisting of (a) a core comprising an active ingredient, where appropriate a carrier and conventional pharmaceutical additives, and the salt of an organic acid whose proportion in the weight of the core amounts to 2.5 to 97.5% by weight, and (b) an outer coating film which consists of one or more (meth)acrylate copolymers and, where appropriate, of conventional pharmaceutical excipients, where 40 to 100% by weight of the (meth)acrylate copolymers consist of 93 to 98% by weight of free-radical polymerized $C_1$ to $C_4$ alkyl esters of acrylic or methacrylic acid and 7 to 2% by weight of (meth)acrylate monomers with a quaternary amino group in the alkyl radical and may where appropriate be present in a mixture, with 1 to 60% by weight of one or more further (meth)acrylate copolymers which are different from the first-mentioned (meth)acrylate copolymers and are composed of 85 to 100% by weight of free-radical polymerized $C_1$ to $C_4$ alkyl esters of acrylic or methacrylic acid and, where appropriate, up to 15% by weight of further (meth)acrylate monomers with basic groups or acidic group in the alkyl radical. Particularly a copolymer of 65 weight percent methyl methacrylate, 30 weight percent ethyl acrylate and 5 weight percent trimethylammoniumethyl methacrylate chloride (EUDRAGIT® RS) or a copolymer of 60 weight percent methyl methacrylate, 30 weight percent ethyl acrylate and 10 weight percent trimethylammoniumethyl methacrylate chloride (EUDRAGIT® RL) is used.

The Machine translation of the unexamined publication KR1996-000227 (Reg. No. KR0128855; Appl. No. KR1994-014987) describes a process for preparing sustained release pellet formulation. Dilitiazem pellets are coated with an aqueous dispersion made from a ready made and commercially available EUDRAGIT® RS 30D dispersion in which stearic acid, arabian gum and sodium lauryl sulfate are dissolved to give the final coating composition.

In US 2008/0152595 A1 methods and compositions for deterring abuse of orally administered pharmaceutical products are described. Dry compositions comprising pharmaceutical active ingredients like oxicodone, EUDRAGIT® RS in powder form, plasticizers and emulsifiers are used to produce controlled release capsules by direct compression. The direct compression compositions are intended for oral ingestion.

Problem and Solution

In respect to dispersions comprising a (meth)acrylate copolymer which is composed of methyl methacrylate, ethylacrylate and 2-trimethylammoniumethyl methacrylate there was no method provided in the technical background which allows the preparation of aqueous dispersions as coating agent or binding agent for oral or dermal pharmaceutical preparations at lower temperatures. Instead, in the prior art the preparation of aqueous dispersions as coating agent or binding agent for oral or dermal pharmaceutical preparations, which dispersion is containing said cationic (meth)acrylate copolymers, the preparation of said dispersion includes a heating step to high temperatures of about 60 to 85° C. which is costly and involves respective complicated devices.

Further, there is a desire for facilitating the preparation of said aqueous dispersions.

Therefore, the object of the present invention was to provide a method for preparing a dispersion as coating agent or binding agent for oral or dermal pharmaceutical preparations, which dispersion is containing a cationic (meth)acrylate copolymer wherein the step of dispersing can be carried out at a lower temperature, namely the object was to provide a method which allows faster and easier preparation of said dispersions.

The technical problem was solved by a process for converting a solid (meth)acrylate copolymer into a dispersed form by preparing an aqueous dispersion comprising the components (a) a (meth)acrylate copolymer which is composed of free-radical polymerized methyl methacrylate, ethylacrylate and a salt of 2-trimethylammoniumethyl methacrylate, present in solid form as a powder or as a granulate, (b) up to 50% by weight calculated on the (meth)acrylate copolymer (a) of a dispersing agent selected from the groups of (b) i) plasticizers in combination with emulsifiers and/or (b) ii) pharmaceutically acceptable carbohydrates having 6 to 18 carbon atoms with a functional group and (c) water by mixing the components (a), (b) and (c) to give a suspension which becomes an aqueous dispersion during the conversion of the solid (meth)acrylate copolymer into the dispersed form, characterized in that,
the (meth)acrylate copolymer is converted into the dispersed form by means of the presence of the dispersing agent at a temperature of less than 50° C.

One of the advantages of the present invention is that ready-to-use dispersions are provided which do not involve costly heating steps for their preparation. The process according to the invention is completely different from so called solvent evaporation processes where large amounts of organic solvents are employed to dissolve certain polymer first before transferring them to aqueous dispersions after removing the organic solvent by evaporation.

Total Composition of the Dispersion

The aqueous dispersion is consisting of water and dry substance (solid content) which add up to 100%. The dry substance of the aqueous dispersion may consist to at least 10, at least, 20 at least, at least 30, at least 40, at least 50, at least, at least 60, at least 70, at least 80, at least 90% by weight of the components (a) and (b) and up to 90, up to 80, up to 70, up to 60, up to 40, up to 30, up to 20, up to 10% by weight of active pharmaceutical, nutraceutical or cosmeceutical ingredients or further pharmaceutical, nutraceutical or cosmeceutical excipients which are different from the components (a) and (b). The components (a) and (b) and if present active pharmaceutical, nutraceutical or cosmeceutical ingredients or the further pharmaceutical, nutraceutical or cosmeceutical excipients which are different from the components (a) and (b) add up to 100% of the solid content of the aqueous dispersion. Most preferably the dry substance of the aqueous dispersion may consist to 100% out of the components (a) and (b).

The solid content of the dispersion may be in the range of 10 to 50, preferably 15 to 40, preferably 15 to 30% by weight based on the total weight of the dispersion. Thus the content of water (c) may be 90 to 50, preferably 85 to 60, preferably 85 to 70% by weight based on the total weight of the dispersion.

Component (a)

Component (a) is a (meth)acrylate copolymer which is composed of free-radical polymerized methyl methacrylate, ethylacrylate and a salt of 2-trimethylammoniumethyl methacrylate. These kind of copolymers may be used for sustained release coating compositions or sustained release matrix compositions.

The Component (a) may be used in the inventive process in solid (dry) form as a powder for instance with an average particle size of 1 to 500 µm or as a granulate with an average particle size above 500 to 5000 µm to become converted into the dispersed form.

Preferably component (a) may be a (meth)acrylate copolymer composed 85-98% by weight of methyl methacrylate and ethyl acrylate and 15 to 2% by weight of a salt of 2-trimethylammoniumethyl methacrylate, preferably, 2-trimethylammoniumethyl methacrylate chloride. The weight percentages add up to 100%.

Further, component (a) may be a (meth)acrylate copolymer composed 50 to 70% by weight of methyl methacrylate, 20 to 40% by weight of ethyl acrylate and 7 to 2% by weight of a salt of 2-trimethylammoniumethyl methacrylate, preferably 2-trimethylammoniumethyl methacrylate chloride (EUDRAGIT® RS type), wherein the weight percentages add up to 100%.

A specifically suitable copolymer comprises 65% by weight of methyl methacrylate, 30% by weight of ethyl acrylate and 5% by weight of 2-trimethylammoniumethyl methacrylate chloride be composed (EUDRAGIT® RS).

Further, component (a) preferably may be a (meth)acrylate copolymer composed 50 to 70% by weight of methyl methacrylate, 20 to 40% by weight of ethyl acrylate and more than 7 up to 12% by weight of a salt of 2-trimethylammoniumethyl methacrylate, preferably 2-trimethylammoniumethyl methacrylate chloride (EUDRAGIT® RL type), wherein the weight percentages add up to 100%.

A specifically suitable copolymer comprises 65% by weight of methyl methacrylate, 30% by weight of ethyl acrylate and 10% by weight of 2-trimethylammoniumethyl methacrylate chloride be composed (EUDRAGIT® RL).

Appropriate (meth)acrylate copolymers are disclosed for example in EP-A 181 515 or DE patent 1 617 751. They are polymers which are soluble or swellable irrespective of the pH and are suitable for medicament coatings. A possible production process to be mentioned is bulk polymerization in the presence of an initiator which forms free radicals and is dissolved in the monomer mixture. The polymer can likewise be produced by means of bulk, solution or precipitation polymerization.

The polymer (a) may be obtained in this way in the form of a fine powder, achievable in the case of bulk polymerization by grinding or milling and in the case of solution and precipitation polymerization for example by spray drying.

Glass Transition Temperatures

The glass transition temperature of said copolymer comprising 65% by weight of methyl methacrylate, 30% by weight of ethyl acrylate and 5% by weight of 2-trimethylammoniumethyl methacrylate chloride be composed (EUDRAGIT® RS) is about 65° C.

The glass transition temperature of said copolymer comprising 60% by weight of methyl methacrylate, 30% by weight of ethyl acrylate and 10% by weight of 2-trimethylammoniumethyl methacrylate chloride (EUDRAGIT® RL) is about 70° C.

The glass transition temperature may be determined as the mean value in the glass transition interval according to DIN ISO 111357 at a heating rate of 20 K/min in the second heat cycle.

By means of the present invention the step of dispersing may be carried out fairly below the glass transition of the copolymers (a) preferably at a temperature below 50° C., more preferred below 45° C., further preferred below 35° C., even more preferred below 30° C. and most preferred at a temperature in the range from 15° C. to 25° C.

Process for Preparing the Copolymer (a)

The preparation of the copolymer by free-radical polymerization of the monomers as such in well-known in the art (see for example EP 0 704 207 and EP 0 704 208). The copolymer may be produced by emulsion polymerization in the aqueous phase in the presence of preferably anionic emulsifiers, for example according to the procedure described in DE-C 2 135 073. Preferred is the production by bulk polymerization.

The copolymer may be produced according to the usual methods of radical polymerization in presence of initiators which form free radicals and optionally in presence of regulators in order to attain a certain molecular weight. The average molecular weight may be from 20,000 to 200,000 (g/mol). Preferably, the copolymer is produced by bulk polymerization.

Dispersing Agent (b)

The dispersing agent (b) may be selected from the groups of a dispersing agent selected from the groups of
(b) i) plasticizers in combination with emulsifiers and/or
(b) ii) pharmaceutically acceptable carbohydrates having 6 to 18 carbon atoms with a functional group Thus the dispersing agent (b) may be selected from either the group (b) i) plasticizers in combination with emulsifiers or from
the group (b) ii) pharmaceutically acceptable carbohydrates having 6 to 18 carbon atoms with a functional group
or from a combination of selected members from group (b) i) and from group (b) ii).

Function of the Dispersing Agent (b)

The presence of the dispersing agent (b) in an amount of up to 50, up to 40, up to 20, preferably 5 to 50% by weight calculated on the (meth)acrylate copolymer (a) is the essential to convert the (meth)acrylate copolymer to become dispersed in water at temperatures of less than 50° C., preferred below 45° C., further preferred below 35° C., even more preferred below 30° C. and most preferred at a temperature in the range from 15° C. to 25° C. (room temperature).

Without the presence of the dispersing agent (b) the (meth) acrylate copolymer will, at temperatures of less than 50° C., remain in water in the form of a suspension and will not become dispersed and thus can not be sufficiently processed to coating and binding agents.

Dispersed means the original solid (meth)acrylate copolymer component (a) which is after the first contact with the water simply suspended in the water becomes more or less uniformly distributed to at least 90, preferably at least 99% to spherically shaped polymer particles with average particles sizes in the range of 50-1000 nm, preferably in the range of 100-500 nm. Most preferred the (meth)acrylate copolymer component (a) becomes more or less completely dispersed to 100% or almost 100%.

Preferably the dispersing process is supported by stirring. Preferably the suspension is stirred to support the distribution of the components (a) and (b) and optionally further excipients in the water. Stirring may be performed using a simple stirrer or a disperser applying high shear forces. Stirring times may be in the range of up to 18 hours (over night), up to 12, up to 8, up to 4 or up to 2 hours. Usually an aqueous dispersion which comprises the (meth)acrylate copolymer component (a) in completely dispersed form can be obtained already within 30 minutes to two hours.

The components (a) and (b) may be added to water (c) in any order, as dry mixed ready to use composition or one as single components together or after another.

Component (b) i) Plasticizers in Combination with Emulsifiers

The process may be carried out in the presence of plasticizers in combination with emulsifiers. Preferably, the content of the plasticizer may be in the range of 1 to 50, preferably in the range of 5 to 40, in the range of 10 to 30% by weight based on the (meth)acrylate copolymer (a) weight. The content of the emulsifier may be in the range of 1 to 30, preferably in the range of 5 to 25% by weight based on the (meth) acrylate copolymer (a) weight.

The component (b) i) may be used alone or in combination with component b ii).

Plasticizers

Plasticizers may influence the functionality of the polymer layer, depending on the type (lipophilic or hydrophilic) and added amount. Plasticizers achieve through physical interaction with the polymers a reduction in the glass transition temperature and promote film formation, depending on the added amount. Suitable substances usually may have a molecular weight of between 100 and 20 000 g/mol and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, diethyl sebacate, dibutyl sebacate and polyethylene glycols 200 to 12 000. Preferred plasticizers are triethyl citrate (TEC), acetyl triethyl citrate (ATEC) and dibutyl sebacate (DBS). Mention should additionally be made of esters which are usually liquid at room temperature, such as citrates, phthalates, sebacates or castor oil. Esters of citric acid and sebacic acid are preferably used.

Addition of the plasticizers to the formulation can be carried out in a known manner, directly, in aqueous solution or after thermal pretreatment of the mixture. It is also possible to employ mixtures of plasticizers.

Emulsifiers

Preferred emulsifiers in respect to component (b) are non-ionic or anionic emulsifiers. Further preferred, the emulsifiers in respect to component (b) may be selected from the group consisting of fatty alkyl sulfates, preferably sodium laurylsulfate, sodium cetylstearylsulfate, saccharose stearate, polysorbates, especially polysorbate 80 (Tween® 80) or mixtures thereof.

Anionic Emulsifers

Examples of suitable anionic emulsifers are
sodium salts of fatty alcohol sulfates, for instance sodium laurylsulfate or sodium cetyl stearylsulfate,
sulfosuccinates, for instance sodium dioctylsulfosuccinate, Nonionic Emulsifiers Examples of suitable nonionic emulsifers are partial esters of fatty acids of polyvalent alcohols for instance glycerine monostearate,
partial esters of fatty acids of sorbitane for instance sorbitan monostearate, sorbitan monooleate, sorbitan sesqui-oleate,
partial esters of fatty acids of polyhydroxy ethylen sorbitan (mono-ester) for instance polyethylen glycol (20)—sorbitan monolaurate, polyethylen glycol (20)—sorbitan monostearate, polyethylen glycol (20)—sorbitan monooleate,
ethers of fattyalcohols and polyhydroxyethylene for instance polyhydroxyethylene-cetylstearyl ether (=Cetomacrogol), polyhydroxyethylene (4)-lauryl ether, polyhydroxyethylene (23)-lauryl ether,
esters of fattyalcohols and polyhydroxyethylene for instance polyhydroxyethylene (8) stearate, polyhydroxyethylene (40) stearate, polyhydroxyethylene (100) stearate,
blockcopolymers of ethylene oxide and propylene oxide for instance condensates of polyhydroxy ethylene and polyhydroxy propylene.

Component (b) ii)

Components (b) ii) are pharmaceutically acceptable carbohydrates having 6 to 18 carbon atoms with a functional group. Preferred are unbranched carbohydrates having 6 to 18 carbon atoms.

The component (b) ii) may be used alone or in combination with component (b) i).

Pharmaceutically acceptable means that the component (b) ii) substances employed shall be toxicologically acceptable and usable in particular in medicaments, nutraceuticals or cosmeceuticals without a risk for patients or customers.

A functional group may be for instance a hydroxyl or a carboxylic acid group. Preferably the functional group is present in the side chain or as a terminal group of the carbohydrates having 6 to 18 carbon atoms. One or more functional groups may be present.

The conponents b ii) may be divided into the further embodiments of the (sub) components (b) ii-i), (b) ii-ii), (b) ii-iii) and (b) ii-iv).

Components (b) ii)-i) to iv)

The process according to the invention may be further characterized in that, the dispersing agent (b) ii) is selected from one or more of the groups consisting of
- (b) ii-i) fatty alcohols having 6 to 18 carbon atoms,
- (b) ii-ii) water soluble salts of saturated or unsaturated carboxylic acids having 6 to 18 carbon atoms,
- (b) ii-iii) unsubstituted mono carboxylic acids having 6 to 18 carbon atoms,
- (b) ii-iv) hydroxycarboxylic acids having 6 to 18 carbon atoms.

Component (b) ii-i) Fatty Alcohols having 6 to 18 Carbon Atoms

Components (b) ii-i) are one or more fatty alcohols having 6 to 18 carbon atoms or mixtures thereof.

In a preferred embodiment the fatty alcohols having 6 to 16 carbon atoms are selected from the group consisting of hexanol, octanol, decanol, dodecanol, tetradecanol or hexadecanol or mixtures thereof, preferably octanol. Preferably, the content of the fatty alcohol is in the range of 1 to 50, 5-40, 8-30% by weight based on copolymer (a) weight.

Component (b) ii-ii) Water Soluble Salts of Saturated or Unsaturated Carboxylic Acids Having 6 to 18 Carbon Atoms Component (b) ii-ii) are one or more water soluble salts of saturated or unsaturated carboxylic acids having 6 to 18 carbon atoms or mixtures thereof.

In a particularly preferred embodiment of the present invention, the salt in respect to component (b) ii-ii) is a salt of a saturated, preferably unbranched, preferably unsubstituted, mono carboxylic acid (fatty acid) having 6 to 18, preferably 8 to 18 or 10 to 16 carbon atoms.

Preferred water soluble salts of saturated or unsaturated carboxylic acids having 6 to 18 carbon atoms in respect to component (b) may be a salt of a carboxylic acid selected from the group consisting of caprylic acid, caprinic acid, lauric acid, myristic acid, palmitic acid, stearic acid, arachidic acid, palmitoleic acid, oleic acid, linoleic acid, linolenic acid, eleostearic acid and arachidonic acid or mixtures thereof. Preferred are alkali metal salts or ammonium salts. Even more preferred are sodium or potassium salts. Most preferred are salts of caprinic acid or stearic acid or mixtures thereof. Preferably, the content of the salt of a carboxylic acid is in the range of 0.1 to 20, preferably 1 to 10% by weight percent based on copolymer (a) weight.

Component (b) ii-iii) Unsubstituted Mono Carboxylic Acids having 6 to 18 Carbon Atoms, Components (b) ii-iii) are one or more unsubstituted mono carboxylic acids having 6 to 18, preferably 6 to 14 carbon atoms or mixtures thereof. Unsubstituted means not substituted in the sense that there are no functional groups present within the molecule except for the carboxyl group.

Preferred unsubstituted mono carboxylic acids having 6 to 14 carbon atoms are saturated. Preferred unsubstituted mono carboxylic acids having 6 to 14 carbon atoms are unbranched.

In another preferred embodiment the saturated or unsaturated carboxylic acid having 6 to 14 carbon atoms, is selected from the group consisting of caproic acid, caprylic acid, caprinic acid, lauric acid, linoleic acid, myristic acid, preferably caprinic acid. Preferably, the content of the carboxylic acid is in the range of 1 to 50, preferably 5-30% by weight percent based on copolymer (a) weight.

Component (b) ii-iv) Hydroxycarboxylic Acids Having 6 to 18 Carbon Atoms

Components (b) ii-iv) are one or more hydroxycarboxylic acids having 6 to 18, preferably 6 to 14 carbon atoms or mixtures thereof.

Preferred hydroxycarboxylic acids having 6 to 18 carbon atoms are for instance citric acid ($C_6H_8O_7$) and ricinoleic acid ($C_{18}H_{34}O_3$).

Further Examples of hydroxycarboxylic acids having 6 to 18 carbon atoms are dihydroxyethylglycine (bicine), 3-hydroxy-4-trimethylammonio-butanoate (carnitine), citric acid, cyclobutyrol, 3-dehydroquinic acid, 2,3-dihydroxy-3-methylpentanoic acid, 2,3-dihydroxybenzoic acid, 2,3-dihydroxymendelic acid, 5-hydroxysalicylic acid (gentisic acid), homocitric acid, isocitric acid, isosaccharinic acid, mandelic acid, mevalonic acid, monatin, pamoic acid, prephenic anid, salicylic acid or shikimic acid.

Preferably, the content of the hydroxycarboxylic acid is in the range of 1 to 50, preferably 5-30% by weight percent based on copolymer (a) weight.

Use of Components (b) ii) in Combination with a Plasticizer

In a preferred embodiment the process according to the invention may be carried out in that one or more of the components b ii) are used in combination with a plasticizer. In this case no emulgator needs to be present. Preferably, the content of the plasticizer may be in the range of 1 to 50, preferably in the range of 5 to 40, in the range of 10 to 30% by weight based on the (meth)acrylate copolymer (a) weight.

Water (c)

The aqueous dispersions described herein may contain 50-90%, up to 50%, up to 60%, up to 70%, up to 80% or up to 90% by weight of water, preferably demineralised water. Water and solids usually add up to 100% whereby components (b) or further excipients which are present and processed in liquid form may be calculated herein simplified as solids. Water shall mean at least 95, at least 97 at least 98 at least 99% or 100% pure water. The water may contain without being crucial for the present invention up to 5, up to 3 up to 2 or up to 1% of organic solvents like ethanol, acetone or isopropanol for instance for the purpose of stabilization against microbial growth or to reduce the surface tension of the dispersion. However, most preferred no organic solvents are present at all.

Further Processing

According to another aspect of the present invention a process is provided for producing pharmaceutical forms, wherein the above method according to the present invention is followed by manufacturing steps wherein the aqueous dispersion is used in pharmaceutically customary processes such as spreading or spraying processes and obtaining the pharmaceutical form.

Details are to be found in the customary textbooks, for example:

Voigt, R. (1984): Lehrbuch der pharmazeutischen Technologie; Verlag Chemie Weinheim—Deerfield Beach/Florida—Basel.

Sucker, H., Fuchs, P., Speiser, P.: Pharmazeutische Technologie, Georg Thieme Verlag Stuttgart (1991), especially Chapters 15 and 16, pp. 626-642.

Gennaro, A. R. (editor), Remington's Pharmaceutical Sciences, Mack Publishing Co., Easton Pa. (1985), Chapter 88, pp. 1567-1573.

List, P. H. (1982): Arzneiformenlehre, Wissenschaftliche Verlagsgesellschaft mbH, Stuttgart.

Ready to Use Composition

The invention also relates to a "ready to use" composition comprising a dry mixture of the components (a) and (b).

The ready to use compositions according to the invention are different from direct compression compositions for instance in the form of matrix tablets or capsule subunits which are intended to be used directly for oral ingestion and which are not intended to be further processed in the form of an aqueous dispersion to be used for creating coating or binding compositions. Thus direct compression compositions for direct oral ingestion such as described in for instance the cited reference US 2008/0152595 A1 may be expressively excluded from the ready to use compositions according to the present invention.

Usually the ready to use composition may be in the form of a powder for instance with an average particle size of 1 to 500 µm or a granulate with an average particle size above 500 to 5000 µm.

A dry mixture shall be understood in the sense that at least the component (a) is present in solid form. The component (b) may be present in solid or in liquid form. If the component (b) is present in liquid form it will be soaked up by the dry component (a) so that in any case the mixture of the components (a) and (b) results in a dry mixture. The compounds may be combined in a solid form and subsequently dried or they may be combined in a melted form, for example by melt extrusion.

The "ready to use" composition may contain at least 20, at least 30, at least, at least 40, at least 50, at least 60, at least 70, at least 80, at least 90, at least 95 or 100% by weight of components (a) and (b). The relation of the component (b) to the component (a) by weight may be from 1:2 to 1:20, preferably from 1:2 to 1:5.

Optionally the "ready to use" composition may additionally comprise pharmaceutical, nutraceutical or cosmetical excipients which are different from the components (a) and (b), for instance pigments or flavours. Usually the "ready to use" composition may comprise or consist of at least 30, at least 50, at least 70, preferably at least 90% by weight of the components (a) and (b) and not more than 70, not more than 50, not more than 30, not more than 10% by weight of pharmaceutical, nutraceutical or cosmetical excipients which are different from the components (a) and (b).

When the "ready to use" composition is mixed with water at a temperature of less than 50° C. preferably below 45° C., more preferred below 35° C., more preferred below 30° C. and most preferred at a temperature in the range from 15° C. to 25° C., it gives first a suspension which later becomes an aqueous dispersion which comprises at least the (meth)acrylate copolymer in dispersed form.

Preferably the suspension is stirred to support the distribution of the components (a) and (b) and optionally further excipients in the water. Usually an aqueous dispersion which comprises the (meth)acrylate copolymer component (a) in completely dispersed form can be obtained already within 30 minutes to two hours.

Use

The present invention also provides the use of an aqueous dispersion originating from the inventive process according as described herein or originating from the inventive ready use composition as described herein as coating agent or binding agent for oral or dermal pharmaceutical, nutraceutical or cosmeceutical preparations. Typical application processes may be wet granulation, spray coating, powder coating, casting, roller coating, blade coating or lamination.

Pharmaceutical, Nutraceutical or Cosmeceutical Excipients

The aqueous dispersions described herein are further characterised in that up to 90, up to 80, up to 70, up to 60, up to 40, up to 30, up to 20, up to 10% by weight, based on the total the solid content respectively the dry weight of the aqueous dispersion, of pharmaceutical, nutraceutical or cosmetical excipients which are different from the components (a), (b) may be contained. However the compositions according to the invention may as well contain any or essentially any pharmaceutical, nutraceutical or cosmetical excipients. Thus the compositions may essentially consist or consist to 100% of the components (a) and (b).

The term pharmaceutical, nutraceutical or cosmeceutical excipient is well known to the skilled person. Such excipients are customary in pharmacy but also in the field of nutraceuticals or cosmetics, occasionally also they are referred as customary additives. It is, of course, always necessary for all the excipients or customary additives employed to be toxicologically acceptable and usable in particular in food or in medicaments without a risk for customers or patients.

Although the requirements are usually higher in the pharmaceutical field there is a widely overlap of excipients used for pharmaceutical purposes and those used for nutraceutical purposes. Usually all pharmaceutical excipients may be used for nutraceutical purposes and at least a large number of nutraceutical excipients are allowed to be used for pharmaceutical purposes as well. Excipients may be are added to the formulation of the invention, preferably during the mixing of the powders production of the granules, for the coating or binding of active ingredients, coating of solids or patches or dispersing semi solids.

Pharmaceutical, nutraceutical or cosmetical excipients with are different from the components (a), (b) and (c) may be contained for practical reasons, for instance to avoid stickiness or to add a colour. However these excipients usually do not contribute or do show any or almost no effect on the invention itself as claimed here.

Pharmaceutical, nutraceutical or cosmetical excipients with are different from the components (a) and (b) do not contribute to the invention in a narrow sense which is based on the interaction of the components (a) and (b). Pharmaceutical, nutraceutical or cosmetical excipients with are different from the components (a), and (b) and which may have an essential adverse effect on the major beneficial effects of the present invention e.g. the preparation time or on the viscosity of the dispersion should be avoided and can be excluded.

Typical pharmaceutical, nutraceutical or cosmetical excipients with are different from the components (a) and (b) are familiar to those skilled in the art. Examples are antioxidants, brighteners, flavouring agents, flow aids for instance silicates like fumed or precipitated silica, fragrances, glidants (release agents), penetration-promoting agents, pigments, polymers, pore-forming agents or stabilizers. They may be used as processing adjuvant and are intended to ensure a reliable and reproducible preparation process as well as good long-term storage stability, or they achieve additional advantageous properties in the pharmaceutical form. They are added to the polymer formulations before processing and can influence the permeability of the coatings. This property can be used if necessary as an additional control parameter.

It is, of course, always necessary for all the pharmaceutical, nutraceutical or cosmetical excipients employed to be toxicologically acceptable and usable in particular in medicaments, nutraceuticals or cosmeceuticals without a risk for patients or customers.

The amounts employed and the use of the pharmaceutical, nutraceutical or cosmetical excipients are familiar to the skilled person. They are added to the polymer preparations before processing and may influence the permeability of the coatings or matrices, it being possible to utilize this where appropriate as additional control parameter.

Release Agents:

Release agents usually have lipophilic properties and are usually added to the spray suspensions. They prevent agglomeration of the cores during the film coating. Talc, Mg stearate or Ca stearate, ground silica or kaolin are preferably employed. The usual amounts employed of release agent are between 0.5 to 100% by weight based on the dry weight of the (meth)acrylate copolymer (a).

Pigments:

Pigments compatible with the coating agent are in particular those pigments which, if added directly to the (meth) acrylate copolymer dispersion, e.g. by stirring in, in the usual amounts used of, for example, 20 to 200% by weight based on the dry weight of the (meth)acrylate copolymer (a), do not lead to destabilization of the dispersion, coagulation, to signs of inhomogeneity or similarly unwanted effects. The pigments to be used are moreover of course non-toxic and suitable for pharmaceutical purposes. Concerning this, see also, for example: Deutsche Forschungsgemeinschaft, *Farbstoffe für Lebensmittel*, Harald, Boldt Verlag K G, Boppard (1978); Deutsche Lebensmittelrundschau 74, No. 4, p. 156 (1978); Arzneimittelfarbstoffverordnung AmFarbV of Aug. 25, 1980.

Pigments may be for example alumina pigments. Further examples of pigments are orange yellow, cochineal red lake, coloured pigments based on alumina or azo dyes, sulphonic acid dyes, orange yellow S (E110, C.I. 15985, FD&C Yellow 6), indigo carmine (E132, C.I. 73015, FD&C Blue 2), tartrazine (E 102, C.I. 19140, FD&C Yellow 5), Ponceau 4R (E 125, C.I. 16255, FD&C Cochineal Red A), quinoline yellow (E 104, C.I. 47005, FD&C Yellow 10), erythrosine (E127, C.I. 45430, FD&C Red 3), azorubine (E 122, C.I. 14720, FD&C Carmoisine), amaranth (E 123, C.I. 16185, FD&C Red 2), acid brilliant green (E 142, C.I. 44090, FD&C Green S).

The E numbers indicated for the pigments relate to an EU numbering. Concerning this, see also "Deutsche Forschungsgemeinschaft, Farbstoffe fër Lebensmittel, Harald Boldt Verlag K G, Boppard (1978); Deutsche Lebensmittelrundschau 74, No. 4, p. 156 (1978); Arzneimittelfarbstoffverordnung AmFarbV of Aug. 25, 1980. The FD&C numbers relate to the approval in food, drugs and cosmetics by the U.S. food and drug administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Polymers

As further excipients polymers different from the (meth) acrylate copolymer (a) or from possible polymeric components (b) may be contained in the aqueous dispersion. However this is meant only for concentrations which do not essentially effect or disturb the basic functions or the basic character of the aqueous dispersion which is mainly caused and determined by the presence of the (meth)acrylate copolymer (a). Thus if further polymers are present, their concentrations are usually lower than that of the (meth)acrylate copolymer (a). Preferably not more than 90%, not more than 50%, not more than 25%, not more than 10%, not more than 5% by weight of such further polymers are contained in relation to the (meth)acrylate copolymer (a). Most preferred no further polymers are contained.

Examples of water soluble polymers may be selected from the group consisting of hydroxypropyl cellulose, hydroxypropyl methylcellulose, and/or polyvinyl alcohol.

Examples of anionic polymeric materials may be selected from the groups consisting of polymethacrylates, cellulose acetate phthalate, polyvinyl acetate phthalate, hydroxypropyl methylcellulose phthalate, hydroxypropyl methylcellulose acetate succinate (HPMC-AS), cellulose acetate trimellitate or Schellack.

Processes for Producing a Pharmaceutical Form (Pellets)

The pharmaceutical form can be produced in a manner known per se by means of usual pharmaceutical processes such as direct compression, compression of dry, wet or sintered granules, extrusion and subsequent rounding off, wet or dry granulation or direct pelleting (e.g. on plates) or by binding of powders (powder layering) onto active ingredient-free beads or cores (nonpareilles) or active ingredient-containing particles, by means of spray processes or fluidized bed granulation. Application in form of a coating can take place by means of known and usual processes such as, for example, spray application of polymer solutions or polymer dispersions.

Nutraceuticals

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flvonoids, antioxidants, alpha-linoleic acid from flax seed, beta-carotene from marigold petals or antocyanins from berries. Sometimes the expression neutraceuticals is used as synonym for nutraceuticals.

Cosmeceuticals

The term "Cosmeceuticals" is used for cosmetic products that are claimed, primarily by those within the cosmetic industry, to have drug-like benefits. Examples of products typically labeled as cosmeceuticals include anti-aging creams and moisturizers. The word is a combination of the words "cosmetic" and "pharmaceutical".

Cosmeceuticals may contain active ingredients such as vitamins, phytochemicals, enzymes, antioxidants, and essential oils. However, these ingredients may not necessarily be effective, and if they are effective, the cosmeceutical may not have the active ingredient(s) in an effective formulation or at effective concentrations.

An important distinction lies in the delivery method. The "cosmeceutical" label applies only to products applied topically, such as creams, lotions, and ointments. Products which are similar in perceived benefits but ingested orally are known as nutricosmetics.

Active Pharmaceutical, Nutraceutical or Cosmeceutical Ingredients

The aqueous dispersion or the ready to use composition may be used as a coating and binding agent in combination with all kinds of pharmaceutical, nutraceutical or cosmeceutical active ingredients. Pharmaceutically, nutraceutically or cosmetically active ingredients have in common that they are active ingredients which have a positive effect on the health of an organism, e. g the human health. They have also in common that their formulations are often the same or very similar. Often also the same kinds of excipients or additives are used in combination with these kinds of active ingredients. Pharmaceutically active ingredients are used to cure diseases and to effect the health of an organism positively, e. g the human health more or less directly. Nutraceutical active ingredients are used to supplement the nutrition and thus support the health of an organism, e. g the human or animal health indirectly. Cosmetically active ingredients are meant to support the human health indirectly for instance by balancing the water content of the human skin.

EXAMPLES

The present invention will be further explained in more detail by the following examples, which are understood not to limit the scope of the invention in any way.

Example 1

EUDRAGIT® RL Dispersion 50.0 g EUDRAGIT® RL was dispersed in 237.2 g demineralized water while stirring with propeller stirrer at room temperature, subsequently added 1.0 g Sodium Caprylate and 8.4 g Dibutylsebacate. After 4.5 hours stirring at 48° C. a low viscose dispersion is obtained. The dispersion is forming a clear, homogenous and glossy film, indicating functionality when dried at room temperature.

Comparative Example 2

EUDRAGIT® RS Dispersion 30.0 g EUDRAGIT® RS was dispersed in 138.0 g demineralized water while stirring on the magnetic stirrer at room temperature, subsequently added with 4.5 g Dibutylsebacate.

After 24 hours a low viscose suspension is obtained with polymer agglomerates. The suspension obtained is not forming a clear homogenous film, indicating missing functionality when dried at room temperature.

Comparative Example 3

EUDRAGIT® RL Dispersion 30.0 g EUDRAGIT® RL was dispersed in 138.0 g demineralized water while stirring on the magnetic stirrer at room temperature, subsequently added with 4.5 g Dibutylsebacate.

After 24 hours a low viscose suspension is obtained with polymer agglomerates. The suspension obtained is not forming a clear homogenous film, indicating missing functionality when dried at room temperature.

Example 4

EUDRAGIT® RS (Powder) Dispersion 15.0 g Polysorbat 80 was dissolved in 580.0 g demineralized water during stirring and 100.0 g EUDRAGIT® RS was added during stirring and subsequently added with 30.0 g triethylcitrate and further stirred at room temperature for further 1 hour.

As stirrer a Ultraturrax, level 1-2 is applied. As result opaque nanopolymeric dispersion is obtained. The dispersion is subjected to a sieving step using a 0.2 mm sieve, wherein 2-3 weight percent non-dispersed retentate is retained in the sieve. The dispersion is forming a very flexible film when dried at room temperature.

Example 5

EUDRAGIT® RS (Powder) Dispersion 20.0 g Polysorbat 80 was dissolved in 680.0 g demineralized water during stirring and 100.0 g EUDRAGIT® RS was added during stirring and subsequently added with 50.0 g triethylcitrate and further stirred at 30° C. for further 1 hour.

As stirrer a Ultraturrax, level 1-2 is applied. As result opaque nanopolymeric dispersion is obtained. The dispersion is forming a clear, very flexible, adhesive film when dried at room temparature.

Example 6

EUDRAGIT® RL Dispersion

In 85.0 g demineralized water 3.0 g Tween® 80 and 6.0 g triethylcitrate were dissolved, 30.0 g EUDRAGIT® RL 100 (particle size 10 μm) was slowly added and further stirred at room temperature.

After having added the polymer completely the viscosity strongly increased. After 1.5 hours the viscosity starts to decrease. After 4 hours an opaque dispersion having low viscosity is obtained. The dispersion is forming a clear and flexible film when dried at room temperature

Example 7

EUDRAGIT® RS Dispersion

In 58.0 g demineralized water 4.5 g Tween® 80 and 7.5 g triethylcitrate were dissolved, 30.0 g EUDRAGIT® RS 100 (particle size 10 μm) was slowly added and further stirred at room temperature.

After having added the polymer completely the viscosity strongly increased. The mixture is added with 1.25 g Ketoprofen and stirred with a spatula for 10 min, however the viscosity remains high. The mixture is diluted to 35% dry weight in order to be able to produce a film. After 1.5 hours of stirring with the spatula the viscosity starts to decrease.

After 4 hours an opaque dispersion having middle viscosity is obtained. The dispersion is forming a tacky, clear and very flexible adhesive film when dried at room temperature

Example 8

EUDRAGIT® RL Dispersion

In 154.2 g demineralized water 7.5 g Polysorbat 80 and 15.0 g TEC were mixed and added with 50.0 g EUDRAGIT® RL PO. After stirring for 2.5 hours at room temperature an opaque dispersion having low viscosity is obtained.

The dispersion is forming a clear, glossy and very flexible film when dried at room temperature.

Example 9

EUDRAGIT® RL Dispersion

In 165.4 g demineralized water 2.31 g Tween® 80 and 4.62 g triethylcitrate were mixed for 2 minutes and 23.07 g EUDRAGIT® RL (particle size 10 μm) was slowly added and further stirred at a temperature starting from 25 to below 50° C.

Once the mixture has reached a temperature of 30° C. the viscosity strongly increased. After 15 minutes no polymer particles could be detected under the microscope. After further 10 minutes the mixture was cooled to room temperature, and a dispersion having low viscosity is obtained which forms a clear, flexible and glossy film dried at room temperature.

Example 10

EUDRAGIT® RS Dispersion Forming an Adhesive Film

In 84.5 g demineralized water 2.14 g Polysorbat 80 and 4.29 g triethylcitrate were stired for 2 min on magnetic stirrer then 8.57 g EUDRAGIT® RS, were added and further stirred. After stirring for 24 hours at room temperature dispersion having low viscosity is obtained which forms a tacky clear film when dried at room temperature.

This adhesive film can not be removed from a glass plate coated with Teflon®.

Example 11

EUDRAGIT® RL Dispersion 30.0 g EUDRAGIT® RL was dispersed in 132.1 g demineralized water while stirring with propeller stirrer at room temperature, subsequently added 18.0 g Polysorbat 80 33.33% and 9.0 g Triethylcitrate.

After 2 hours stirring at 48° C. a low viscose dispersion is obtained. The dispersion is forming a clear, very flexible, homogenous and glossy film, indicating functionality when dried at room temperature.

Example 12

EUDRAGIT® RL Dispersion 50.0 g EUDRAGIT® RL powder was dispersed in 230.0 g demineralized water while stirring with propeller stirrer at room temperature, subsequently added 15.0 g Polysorbat 80 33.33% and 5.0 g Triethylcitrate.

After 2 hours stirring at 48° C. a low viscose dispersion is obtained. The dispersion is forming a clear, homogenous and glossy film, indicating functionality when dried at room temperature.

Example 13

EUDRAGIT® RL Dispersion 50.0 g EUDRAGIT® RL 100 granules were dispersed in 230.0 g demineralized water while stirring with propeller stirrer at room temperature, subsequently added 15.0 g Polysorbat 80 33.33% and 5.0 g Triethylcitrate.

After 3 hours stirring at 48° C. a low viscose dispersion is obtained. The dispersion is forming a clear, homogenous and glossy film, indicating functionality when dried at room temperature.

Example 14

EUDRAGIT® RL Dispersion 10.0 g Polysorbat 80 10.0 g triethylcitrat were mixed for 5 min in 480.0 g demineralized water while stirring with propeller stirrer at room temperature, subsequently 100.0 g EUDRAGIT® RL added.

After 2 hour stirring at 45° C. dispersion is obtained which is forming a clear flexible film when dried at room temperature or 40° C.

To this dispersion a mixture of 12 g HPMC, 18.0 g Mg. stearat and 120.0 g demineralised water was added and stirred for 2 hours. The HPMC-Mg-Stearat suspension was poured during stirring to the RL dispersion and further stirred for 1 hour.

Then the Dispersion-suspension was freeze-dried.

40.0 g of freeze-dried product were redispersed in 160 g dem. water by gentle stirring with propeller stirrer at room temperature. The "ready to use" spray-suspension was applied on Diprophylline pellets without any problems. An immediate release coating was obtained with 20% applied on dry substance.

Example 15

EUDRAGIT® RL Dispersion 30.0 g EUDRAGIT® RL was dispersed in 144.0 g demineralized water 3.0 g PS 80 while stirring on the magnetic stirrer at room temperature, subsequently added with 6.0 g Glycerol, after 1 hour stirring 6 g ATBC was added.

After further 2 hours stirring a low viscose dispersion is obtained. The dispersion suspension is forming a clear, flexible homogenous and glossy film, indicating functionality when dried at room temperature.

Example 16

EUDRAGIT® RL Dispersion 30.0 g EUDRAGIT® RL (powder) was dispersed in 132.0 g demineralized water while stirring on the magnetic stirrer at room temperature, subsequently added with 9.0 g Polysorbat 80 33.5% solution and 1.5 g ATEC.

After 2.5 hours stirring at 45° C. a low viscose dispersion is obtained. The dispersion suspension is forming a clear, glossy film, indicating functionality when dried at room temperature.

Example 17

EUDRAGIT® RS Dispersion 43.0 g EUDRAGIT® RS (powder) was dispersed in 165.0 g demineralized water while stirring on the magnetic stirrer at room temperature, subsequently added with 13.5 g Polysorbat 80 and 9.0 g ATBC.

After 6 hours stirring at 48° C. a low viscose dispersion is obtained. The dispersion suspension is forming a clear, very flexible and glossy film, indicating functionality when dried at room temperature.

Example 18

EUDRAGIT® RL (Powder) Dispersion 20.0 g of a homogeneous mixture of 70.4% EUDRAGIT® RL PO, 10.6% stearic acid, 4.9% SDS, 7.0% talc, and 7.0% pigment Candurin, was added during stirring at room temperature to 113.3 g demineralized water and stirred for 20 min. then the temperature was increased to 48° C. After 2.5 hours the mixture was homogenized with Ultra Turrax for 5 min, a homogeneous dispersion-suspension was formed, a nanopolymeric dispersion is obtained. The dispersion is subjected to a sieving step using a 0.2 mm sieve, wherein 0.2 weight percent non-dispersed retentate is retained in the sieve. The dispersion is forming a flexible film when dried at room temperature.

Comparative Example 19

EUDRAGIT® RS (Powder) Dispersion 10.0 g SDS was dissolved in 256.7 g demineralized water during stirring and 100.0 g EUDRAGIT® RS was added during stirring and further stirred at room temperature for further 24 hour. As stirrer a propeller stirrer is applied. As result no opaque nanopolymeric dispersion is obtained. The suspenion is no forming a film when dried at room temperature.

Comparative Example 20

EUDRAGIT® RL Dispersion 1.5 g SDS was dissolved in 60 g demineralized water while stirring on the magnetic stirrer, subsequently added with 15.0 g EUDRAGIT® RL (powder) and then heated to 65° C.

After stirring for 48 hours the suspension has a low viscosity. And is forming a white, very brittle and fissured mass, indicating missing functionality when dried at room temperature or 40° C.

Example 21

EUDRAGIT® RS (Powder) Dispersion 10.0 g SDS was dissolved in 520.0 g demineralized water during stirring and 100.0 g EUDRAGIT® RS was added during stirring and subsequently added with 20.0 g dibuthylsebacat and further stirred at room temperature for further 1 hour.

As stirrer a Ultraturrax, level 1 is applied. As result opaque nanopolymeric dispersion is obtained. The dispersion is subjected to a sieving step using a 0.2 mm sieve, wherein <1 weight percent non-dispersed retentate is retained in the sieve. The dispersion is forming a flexible film when dried at room temperature.

Example 22

EUDRAGIT® RS Dispersion

In 85.0 g demineralized water 10.34 g EUDRAGIT® RS (powder), 1.55 g SDS and 3.1 g dibuthylsebacat were added and stirred on the magnetic stirrer. After stirring over night at room temperature, a dispersion having low viscosity is obtained which forms a flexible, clear slightly sticky film when dried at room temperature or 40° C.

Example 23

EUDRAGIT® RS (Powder) Dispersion

In 85.0 g demineralized water 1.83 g SDS 2.42 g dibuthylsebacat were mixed for 2 minutes and 10.75 g EUDRAGIT® RS, were added and stirred on the magnetic stirrer. After stirring for 24 hours at room temperature dispersion having low viscosity is obtained which forms a flexible, film when dried at room temperature or 40° C.

Example 24

EUDRAGIT® RS (Powder) Dispersion

In 85.0 g demineralized water 1.73 g SDS and 1.73 g dibuthylsebacat were mixed for 2 minutes then 11.54 g EUDRAGIT® RS were added and stirred on the magnetic stirrer. After stirring for 24 hours at room temperature dispersion having low viscosity is obtained which forms a flexible, clear film when dried at room temperature or 40° C.

Example 25

EUDRAGIT® RS Dispersion

In 140.0 g demineralized water 41.38 g EUDRAGIT® RS, 6.21 g SDS and 12.41 g dibuthylsebacat were added and stirred on the magnetic stirrer. After stirring for 24 hours at room temperature dispersion having low viscosity is obtained having a content of 30 weight percent dry weight which forms a very flexible, clear to cloudy film when dried at room temperature or 40° C.

Example 26

Eudragit® RS (Powder) Dispersion 15.0 g Sodium dodecylsulfate (SDS) was dissolved in 338.3 g demineralized water during stirring and 100.0 g EUDRAGIT® RS was added during stirring and subsequently added with 30.0 g diethylsebacat and further stirred at room temperature for further 2-3 hours.

As stirrer a rotating disk (German expression: "Dissolverscheibe") is applied which is run at 600 rpm. As result opaque nanopolymeric dispersion is obtained. The dispersion is subjected to a sieving step using a 0.2 mm sieve, wherein 2 weight percent non-dispersed retentate is retained in the sieve. The dispersion is forming a soft and flexible film when dried at room temperature.

Example 27

EUDRAGIT® RS (Powder) Dispersion 10.0 g Sodium dodecylsulfate (SDS) was dissolved in 520.0 g demineralized water during stirring and 100.0 g EUDRAGIT® RS was added during stirring and subsequently added with 20.0 g diethylsebacat and further stirred at room temperature for further 2 hour.

As stirrer an Ultraturrax, level 1 is applied. As result opaque nanopolymeric dispersion is obtained. The dispersion is subjected to a sieving step using a 0.2 mm sieve, wherein 4 weight percent non-dispersed retentate is retained in the sieve. The dispersion is forming a clear flexible film when dried at room temperature.

Example 28

EUDRAGIT® RL (Powder) Dispersion 20.0 g of a homogeneous mixture of 69.7% RL PO, 13.9% PEG 6000, 2.4% SDS, 7.0% talc, and 7.0% pigment Candurin, was added during stirring at room temperature to 113.3 g demineralized water and stirred for 20 min. then the temperature was increased to 48° C.

After 2.5 hours a homogeneous dispersion-suspension was formed, a nanopolymeric dispersion is obtained. The dispersion is subjected to a sieving step using a 0.2 mm sieve, wherein 0.2 weight percent non-dispersed retentate is retained in the sieve. The dispersion is forming a glossy film when dried at room temperature.

Example 28A

Eudragit® RL (Powder) Dispersion 3.3 g Sodium dodecylsulfate (SDS) was dissolved in 480.0 g demineralized water during stirring and 100.0 g EUDRAGIT® RL was added during stirring and subsequently added with 16.7 g dibuthylsebacat and further stirred at 48° C. for further 2-3 hours.

As stirrer a rotating disk (German expression: "Dissolverscheibe") is applied which is run at 600 rpm. As result opaque nanopolymeric dispersion is obtained. The dispersion is subjected to a sieving step using a 0.2 mm sieve, wherein 1 weight percent non-dispersed retentate is retained in the sieve. The dispersion is forming a clear flexible film when dried at room temperature.

Example 29

EUDRAGIT® RS Dispersion 30.0 g EUDRAGIT® RS was dispersed in 165, 8.0 g demineralized water while stirring on the magnetic stirrer at room temperature, subsequently added with 2.4 g Cetylalcohol, 6.0 g Caprylic acid and 3.0 Polysorbat 80.

After 24 hours stirring at 45° C. a low viscose dispersion is obtained. The dispersion suspension is forming a white, flexible and film, when dried at room temperature.

Example 30

EUDRAGIT® RL Dispersion 30.0 g EUDRAGIT® RL was dispersed in 129.6 g demineralized water while stirring on the magnetic stirrer at room temperature, subsequently added with 2.4 g Decanol.

After 1 hour stirring at 45° C. a low viscose dispersion is obtained. The dispersion suspension is forming a clear, homogenous and glossy film, indicating functionality when dried at room temperature.

Example 31

EUDRAGIT® RL Dispersion 25.0 g EUDRAGIT® RL was dispersed in 108.0 g demineralized water while stirring on the magnetic stirrer at room temperature, subsequently added with 2.0 g Hexanol.

After 2 hours stirring at 40° C. a low viscose dispersion is obtained. The dispersion suspension is forming a clear, homogenous and glossy film, indicating functionality. when dried at room temperature.

Example 32

EUDRAGIT® RL Dispersion 50.0 g EUDRAGIT® RL was dispersed in 140.0 g demineralized water while stirring with propeller stirrer, subsequently 10.0 g 1-Octanol was added while stirring at room temperature.

After 10 min a high viscous gel was formed. 200.0 g water was added and further stirred for 2 hours. A dispersion having low viscosity is obtained and is forming a clear, flexible and glossy film, indicating functionality, when dried at room temperature.

Example 33

EUDRAGIT® RL Dispersion 50.0 g EUDRAGIT® RL was dispersed in 128.33 g demineralized water while stirring with propeller stirrer, subsequently 5.0 g 1-Octanol was added while stirring at room temperature.

After 10 min a high viscous gel was formed. 91.7 g water was added and further stirred for 5 hours. A dispersion having low viscosity is obtained and is forming a clear, flexible and glossy film, indicating functionality, when dried at room temperature.

Example 34

EUDRAGIT® RS Dispersion 20.0 g EUDRAGIT® RS was dispersed in 56.0 g demineralized water while stirring on the magnetic stirrer, subsequently 4.0 g Lactic acid was added while stirring at room temperature.

After 3 hours stirring at 6.0 g caprylic acid was added and further stirred for 2 hours. Then the temperature was increased to 40° C. and over night (app. 12 h) a dispersion having low viscosity is obtained and is forming a clear, flexible and glossy film, indicating functionality, when dried at room temperature.

Comparative Example 35

EUDRAGIT® RL Dispersion 30.0 g EUDRAGIT® RL was dispersed in 144.0 g demineralized water while stirring on the magnetic stirrer at room temperature, subsequently added with 6.0 g Behenic acid.

After 48 hour stirring at 45° C. a suspension is obtained. The suspension is forming not forming a film when dried at room temperature or 40° C.

Example 36

EUDRAGIT® RL Dispersion 30.0 g EUDRAGIT® RL was dispersed in 144.0 g demineralized water while stirring with propeller stirrer at room temperature, subsequently added 3.0 g Caprylic acid and 3.0 g Stearic acid.

After 3 hours stirring at 48° C. a low viscose dispersion is obtained. The dispersion is forming a clear, homogenous and glossy film, indicating functionality when dried at room temperature.

Example 37

EUDRAGIT® RL Dispersion 30.0 g EUDRAGIT® RL was dispersed in 91.0 g demineralized water while stirring on the magnetic stirrer, subsequently 9.0 g Caprylic acid was added while stirring at room temperature.

A dispersion having low viscosity is obtained within 50 minutes. The dispersion obtained is forming a clear, flexible and glossy film, indicating functionality, when dried at room temperature.

Example 38

EUDRAGIT® RS Dispersion 20.0 g EUDRAGIT® RS was dispersed in 53.7 g demineralized water while stirring on the magnetic stirrer, subsequently 3.0 g Lutrol F 127 was added while stirring at room temperature.

After 3 hours stirring at 6.0 g Caprylic acid was added and further stirred for 2 hours. Then the temperature was increased to 40° C. and over night (app. 12 h) a 35.4% dispersion with very few RS-particles is obtained and is forming a clear, flexible and glossy film, indicating functionality, when dried at room temperature.

Example 39

EUDRAGIT® RL Dispersion 30.0 g EUDRAGIT® RL was dispersed in 156.0 g demineralized water while stirring on the magnetic stirrer, subsequently 9.0 g Caprylic acid was added while stirring at room temperature.

A dispersion having low viscosity is obtained within 30 minutes. The dispersion obtained is forming a clear, flexible and glossy film, indicating functionality, when dried at room temperature.

Example 40

EUDRAGIT® RL Dispersion 20.0 g EUDRAGIT® RL was dispersed in 80.0 g demineralized water while stirring with propeller stirrer at room temperature, subsequently added with 2.0 g Hydroxypropylmethylcellulose (Methocel E5).

After 10 min stirring at room temperature 3.0 g Caprylic acid was added and further stirred at room temperature for 3 hours. A low viscous dispersion was formed, which is forming a clear, flexible and glossy film, when dried at room temperature.

Example 41

EUDRAGIT® RL Dispersion 20.0 g EUDRAGIT® RL was dispersed in 96.0 g demineralized water while stirring on the magnetic stirrer, subsequently 4.0 g Caprylic acid was added while stirring at room temperature.

A dispersion having low viscosity is obtained within 30 minutes. The dispersion obtained is forming a clear, flexible and glossy film, indicating functionality, when dried at room temperature.

Example 42

EUDRAGIT® RL Dispersion 30.0 g EUDRAGIT® RL was dispersed in 126.0 g demineralized water while stirring with propeller stirrer at room temperature, subsequently added 9.0 g Citric acid.

After 1.5 hours stirring at 48° C. a low viscose dispersion is obtained. The dispersion suspension is forming a clear, homogenous and glossy film, indicating functionality when dried at room temperature.

Comparative Example 43

EUDRAGIT® RS Dispersion 30.0 g EUDRAGIT® RS was dispersed in 91.0 g demineralized water while stirring with propeller stirrer at room temperature, subsequently added 9.0 g Citric acid.

After 4 hours stirring at 60+80° C. a high viscose white gel is obtained. The dispersion suspension is forming a clear, homogenous and glossy film, indicating functionality when dried at room temperature.

Example 44

EUDRAGIT® RL Dispersion 50.0 g EUDRAGIT® RL was dispersed in 240.0 g demineralized water while stirring with propeller stirrer at room temperature, subsequently added 10.0 g Citric acid.

After 3 hours stirring at 40° C. a low viscose dispersion is obtained. The dispersion is forming a clear, homogenous and glossy film, indicating functionality when dried at room temperature.

Example 45

EUDRAGIT® RL Dispersion 50.0 g EUDRAGIT® RL was dispersed in 340.0 g demineralized water while stirring with propeller stirrer at room temperature, subsequently added 10.0 g Lauric acid.

After 5 hours stirring at 45° C. a low viscose dispersion is obtained. The dispersion is forming a clear, homogenous and glossy film, indicating functionality when dried at room temperature.

Example 46

EUDRAGIT® RL Dispersion 30.0 g EUDRAGIT® RL was dispersed in 132.0 g demineralized water while stirring on the magnetic stirrer, subsequently 0.4 g Linoleic acid was added while stirring at 45° C.

A dispersion having middle viscosity is obtained within 3 hours. The dispersion obtained is forming a clear and glossy film, indicating functionality, when dried at room temperature.

Example 47

EUDRAGIT® RL Dispersion 50.0 g EUDRAGIT® RL was dispersed in 237.2 g demineralized water while stirring with propeller stirrer at room temperature, subsequently added 1.0 g Sodium caprylate and 8.4 g Caprylic acid.

After 2 hours stirring at 48° C. a low viscose dispersion is obtained. The dispersion is forming a clear, homogenous and glossy film, indicating functionality when dried at room temperature.

Example 48

EUDRAGIT® RL Dispersion 2.0 g Sodium Caprylate 17.0 g Caprylic acid were mixed for 5 min in 480.0 g demineralized water while stirring with propeller stirrer at room temperature, subsequently 100.0 g EUDRAGIT® RL added.

After 2 hour stirring at 45° C. dispersion is obtained which is forming a clear flexible film when dried at room temperature or 40° C.

To this dispersion a mixture of 6.0 g HPMC, 17.1 g Glyceroltristearate 92.4 g demineralised water was added and stirred for 1 hour. The HPMC-Glyceroltristearate-suspension was poured during stirring to the RL dispersion and further stirred for 1 hour.

Then the Dispersion-suspension was freeze-dried.

40.0 g of freeze-dried product were redispersed in 160 g dem. Water by gentle stirring with propeller stirrer at room temperature. The "ready to use" spray-suspension was applied on Diprophylline pellets without any problems. An immediate release coating was obtained with 20% applied on dry substance

Example 49

EUDRAGIT® RL Dispersion 2.0 g Sodium Caprylate 17.0 g Caprylic acid were mixed for 5 min in 480.0 g demineralized water while stirring with propeller stirrer at room temperature, subsequently 100.0 g EUDRAGIT® RL added.

After 2 hour stirring at 45° C. dispersion is obtained which is forming a clear flexible film when dried at room temperature or 40° C.

To this dispersion a mixture of 11.8 g HPMC, 11.8 g AEROSIL® 200 94.4 g demineralised water was added and stirred for 1 hour. The HPMC-AEROSIL200-suspension was poured during stirring to the RL dispersion and further stirred for 1 hour.

Then the Dispersion-suspension was freeze-dried.

40.0 g of freeze-dried product were redispersed in 160 g dem. Water by gentle stirring with propeller stirrer at room temperature. The "ready to use" spray-suspension was applied on Diprophylline pellets without any problems. An immediate release coating was obtained with 20% applied on dry substance

Example 50

EUDRAGIT® RL Dispersion 30.0 g EUDRAGIT® RL was dispersed in 144.0 g demineralized water while stirring on the magnetic stirrer at room temperature, subsequently added with 6.0 g Ricinoleic acid.

After 2 hour stirring at 40° C. a low viscose dispersion is obtained. The dispersion suspension is forming a clear, homogenous and glossy film, indicating functionality when dried at room temperature.

Comparative Example 51

EUDRAGIT® RL Dispersion 30.0 g EUDRAGIT® RL was dispersed in 186.0 g demineralized water while stirring on the magnetic stirrer at room temperature, subsequently added with 16.5 g Stearic acid.

After 48 hour stirring at 45° C. a suspension is obtained. The suspension is forming not forming a film when dried at room temperature or 40° C.

Comparative Example 52

EUDRAGIT® RS Dispersion 30.0 g EUDRAGIT® RS was dispersed in 213.6 g demineralized water while stirring on the magnetic stirrer at room temperature, subsequently added with 14.4 g Tartaric acid and 9.0 g TEC.

After 24 hours stirring at 45° C. a low viscose dispersion is obtained. The dispersion suspension is forming a white film, when dried at room temperature.

Comparative Example 53

EUDRAGIT® RL Dispersion 20.0 g EUDRAGIT® RL was dispersed in 80.0 g demineralized water while stirring with propeller stirrer at room temperature, subsequently added with 2.0 g Hydroxypropylmethylcellulose (Methocel E5).

After 30 min stirring at room temperature nothing changed so the temperature was increased to 45° C. and further to 65° C. and then to 90° C. Between 1 h at this temperature the viscosity increased and decreases slowly during stirring further 4 hours. The dispersion is forming a clear, very brittle film, when dried at room temperature.

Example 54

EUDRAGIT® RS-RL Spray-Coating and Release Tests 117.0 g of Example 24 was stirred and 9.73 of Example 28A was added. Further 10.0 g Magnesium-stearate was dispersed by Ultra Turrax fpor 10 min in 42.3 g dem water. The Mg-Stearat-suspension was poured to the RS-RL-dispersion dispersion.

150 g Theophylline pellets (1.0 to 1.25 mm in size) were coated in a Hüttlin Mycrolab device using the dispersions-suspension prepared in this example. Table 1 summarizes the coating conditions for theophylline pellets.

TABLE 1

| coating conditions for theophylline pellets. | |
|---|---|
| Formulation | Example 54 |
| inlet temperature (° C.) | 45 |
| bed temperature (° C.) | 30-33° C. |
| outlet temperature (° C.) | 26-29 |
| air flow rate (m³/h) | 16-18 m³/h |
| Nozzle bore (mm) | 0.8 |
| atomizing pressure (bar) | 0.8 |
| spray rate (ml/min) | 1.3-2.2 |

The spraying time for 10 percent weight gain based on polymer weight was 68 minutes (179.0 g of the dispersions obtained according to example 54). The coated pellets obtained by the spraying process were tested for release of theophylline. The dissolution test for coated pellets comprising as active ingredient theophylline, were carried out using BP Method II paddle apparatus (Model PTWS, Pharmatest, Hainburg, Germany). The volume of the dissolution media was 900 ml maintained at 37+0.5° C. and a paddle speed of 100 rpm was employed. The amount of theophylline released from the coated tablets or pellets was determined by UV spectrophotometer at 271 nm for theophylline. The pellets were placed for 120 min into 0.1N HCl, Example of sustained release coated Theophylline pellets with 10% w/w on polymer formulation in comparison with standard: The (comparative) example in the left column is based on a commercially available EUDRAGIT® RS, EUDRAGIT® RL dispersion respectively (EUDRAGIT® RS 30D/EUDRAGIT® RL 30D). The example in the right column is an inventive example where the aqueous dispersion is made from EUDRAGIT® RS and EUDRAGIT® RL powder.

|  |  | Composition | |
|---|---|---|---|
|  |  | 90% EUDRAGIT® RS (dry weight) 10% EUDRAGIT® RL (dry weight) +20% Triethyl citrat (TEC) +50% Talc Drug release [%] 0,1N HCl | 90% EUDRAGIT® RS PO 10% EUDRAGIT® RL PO +13.9% SDS +15.2% DBS +50% Talc Drug release [%] 0,1N HCl |
| Media | [min] | | |
| 0,1N HCl | 0 | −0.02 | 0.05 |
| 0,1N HCl | 30 | 0.31 | 0.33 |
| 0,1N HCl | 60 | 0.80 | 1.52 |
| 0,1N HCl | 90 | 1.44 | 3.03 |
| 0,1N HCl | 120 | 2.20 | 4.80 |

Example 55

Theophyllin pellets were coated in a fluidized bed coater using the dispersion of examples 14 and 48 applying similar coating conditions as in example 54. After drying the pellets were coated homogeneously with a glossy film. Drug release [%] was tested similar to example 54 in demineralized water and 0.1N HCl.
(RLPO=EUDRAGIT® RL (Powder))

|  | Example 14 | Example 48 | Example 14 | Example 48 |
|---|---|---|---|---|
|  |  | Composition | | |
|  | 66. % RLPO 6.7% TEC 6.7% PS80 12.0% Mg-stearat 8.0% HPMC Drug release [%] dem. water | 70.0% RLPO 1.4% Na-Caprylate 11.8% Caprylic acid 12.5% Glycerol-tristearate 4.2% HPMC Drug release [%] dem. water | 66./% RLPO 6.7% TEC 6.7% PS80 12.0% Mg-stearat 8.0% HPMC Drug release [%] 0.1NHCl | 70.0% RLPO 1.4% Na-Caprylate 11.8% Caprylic acid 12.5% Glycerol-tristearate 4.2% HPMC Drug release [%] 0.1NHCl |
| [min] | | | | |
| 0 | −0.12 | 0.00 | 0.01 | −0.01 |
| 5 | 44.95 | 48.10 | 56.20 | 40.50 |
| 15 | 99.32 | 97.81 | 99.08 | 97.51 |
| 30 | 99.90 | 99.23 | 100.04 | 99.25 |
| 45 | 99.79 | 99.44 | 99.79 | 99.48 |
| 60 | 99.91 | 99.66 | 99.72 | 99.16 |
| 90 | 100.00 | 100.00 | 100.00 | 100.00 |

The invention claimed is:

1. A ready to use composition, comprising a dry mixture of:
    (a) a (meth)acrylate copolymer comprising, in free-radical polymerized form, methyl methacrylate, ethyl acrylate and a salt of 2-trimethylammoniumethyl methacrylate, wherein the (meth)acrylate copolymer is a solid powder or a solid granulate; and
    (b) up to 50% by weight, based on the (meth)acrylate copolymer (a), of at least one dispersing agent selected from the group consisting of
        (b)(i) a combination comprising a plasticizer and an emulsifier, and
        (b)(ii) a fatty alcohol comprising 6 to 18 carbon atoms, a water soluble salt of a saturated or unsaturated carboxylic acid comprising 6 to 18 carbon atoms, an unsubstituted mono carboxylic acid comprising 6 to 18 carbon atoms, a hydroxycarboxylic acid comprising 6 to 18 carbon atoms, or any mixture thereof,
    wherein:
        the ready to use composition is in the form of a powder or a granulate;
        the powder or granulate of the ready to use composition is not formed by a solvent evaporation process in which one or more organic solvent is combined with a mixture of (a) and (b) before removing the one or more organic solvent by evaporation; and
        when the ready to use composition is mixed with water at a temperature of less than 50° C., an aqueous dispersion is obtained that comprises at least the (meth)acrylate copolymer (a) in dispersed form.

2. The ready to use composition of claim 1, wherein the dispersing agent (b) further comprises a plasticizer.

3. The ready to use composition of claim 1, wherein the dispersing agent (b) comprises at least one plasticizer selected from the group consisting of an alkyl citrate, a glycerol ester, an alkyl phthalate, an alkyl sebacate, a sucrose ester, a sorbitan ester, diethyl sebacate, dibutyl sebacate, triethyl citrate, acetyl triethyl citrate, diethylphthalate and a polyethylene glycol.

4. The ready to use composition of claim 1, wherein the dispersing agent (b) comprises at least one emulsifier selected from the group consisting of a fatty alkyl sulfate, sodium laurylsulfate, sodium cetylstearylsulfate, saccharose stearate, and a polysorbate.

5. The ready to use composition of claim 1, wherein the dispersing agent (b) comprises at least one fatty alcohol selected from the group consisting of hexanol, octanol, decanol, dodecanol, tetradecanol and hexadecanol.

6. The ready to use composition of claim 1, wherein the dispersing agent (b) comprises at least one water soluble salt of a carboxylic acid selected from the group consisting of caprylic acid, caprinic acid, lauric acid, myristic acid, palmitic acid, stearic acid, arachidic acid, palmitoleic acid, oleic acid, linoleic acid, linolenic acid, eleostearic acid, and arachidonic acid.

7. The ready to use composition of claim 1, wherein the dispersing agent (b) comprises at least one unsubstituted mono carboxylic acid selected from the group consisting of caproic acid, caprylic acid, caprinic acid, lauric acid, linoleic acid, and myristic acid.

8. The ready to use composition of claim 1, wherein the dispersing agent (b) comprises at least one hydroxycarboxylic acid selected from the group consisting of dihydroxyethylglycine, 3-hydroxy-4-trimethylammonio-butanoate, citric acid, cyclobutyrol, 3-dehydroquinic acid, 2,3-dihydroxy-3-methylpentanoic acid, 2,3-dihydroxybenzoic acid, 2,3-dihydroxymendelic acid, 5-hydroxysalicylic acid (gentisic acid), homocitric acid, isocitric acid, isosaccharinic acid, mandelic acid, mevalonic acid, monatin, pamoic acid, prephenic acid, ricinoleic acid, salicylic acid, and shikimic acid.

9. The ready to use composition of claim 1, wherein the (meth)acrylate copolymer (a) comprises 85-98% by weight of a $C_1$- to $C_4$-alkylester of methacrylic acid and 15 to 2% by weight of a salt of 2-trimethylammoniumethyl methacrylate.

10. The ready to use composition of claim 1, wherein the ready to use composition is formed by freeze drying an aqueous suspension of a mixture comprising the (meth)acrylate copolymer (a) and the dispersing agent (b).

11. A process for converting a solid (meth)acrylate copolymer into a dispersed form, the process comprising contacting the ready to use composition of claim 1 with water to obtain an aqueous dispersion, wherein the process occurs at a temperature of less than 50° C.

12. The process of claim 11, wherein the dispersing agent (b) further comprises a plasticizer.

13. The process of claim 11, wherein the dispersing agent (b) of the ready to use composition comprises at least one plasticizer selected from the group consisting of an alkyl citrate, a glycerol ester, an alkyl phthalate, an alkyl sebacate, a sucrose ester, a sorbitan ester, diethyl sebacate, dibutyl sebacate, triethyl citrate, acetyl triethyl citrate, diethylphthalate and a polyethylene glycol.

14. The process of claim 11, wherein the dispersing agent (b) of the ready to use composition comprises at least one emulsifier selected from the group consisting of a fatty alkyl sulfate, sodium laurylsulfate, sodium cetylstearylsulfate, saccharose stearate, and a polysorbate.

15. The process of claim 11, wherein the dispersing agent (b) of the ready to use composition comprises at least one fatty alcohol selected from the group consisting of hexanol, octanol, decanol, dodecanol, tetradecanol and hexadecanol.

16. The process of claim 11, wherein the dispersing agent (b) of the ready to use composition comprises at least one water soluble salt of a carboxylic acid selected from the group consisting of caprylic acid, caprinic acid, lauric acid, myristic acid, palmitic acid, stearic acid, arachidic acid, palmitoleic acid, oleic acid, linoleic acid, linolenic acid, eleostearic acid, and arachidonic acid.

17. The process of claim 11, wherein the dispersing agent (b) of the ready to use composition comprises at least one unsubstituted mono carboxylic acid selected from the group consisting of caproic acid, caprylic acid, caprinic acid, lauric acid, linoleic acid, and myristic acid.

18. The process of claim 11, wherein the dispersing agent (b) of the ready to use composition comprises at least one hydroxycarboxylic acid selected from the group consisting of dihydroxyethylglycine, 3-hydroxy-4-trimethylammonio-butanoate, citric acid, cyclobutyrol, 3-dehydroquinic acid, 2,3-dihydroxy-3-methylpentanoic acid, 2,3-dihydroxybenzoic acid, 2,3-dihydroxymendelic acid, 5-hydroxysalicylic acid (gentisic acid), homocitric acid, isocitric acid, isosaccharinic acid, mandelic acid, mevalonic acid, monatin, pamoic acid, prephenic acid, ricinoleic acid, salicylic acid, and shikimic acid.

19. The process of claim 11, wherein the (meth)acrylate copolymer (a) of the ready to use composition comprises 85-98% by weight of a $C_1$- to $C_4$-alkylester of methacrylic acid and 15 to 2% by weight of a salt of 2-trimethylammoniumethyl methacrylate.

20. A coating agent or a binding agent comprising an aqueous dispersion obtained by contacting the ready to use composition of claim 1 with water,
wherein:
the contacting occurs at a temperature of less than 50° C.; and
the coating agent or the binding agent is suitable for oral or dermal pharmaceutical, nutraceutical or cosmeceutical preparations.

21. The process of claim 11, comprising contacting the (meth)acrylate copolymer (a), and 5 to 50% by weight, based on the (meth)acrylate copolymer (a), of the dispersing agent (b), with the water (c).

22. The process of claim 11, wherein a dry substance of the aqueous dispersion comprises the (meth)acrylate copolymer (a), the dispersing agent (b), and at least one selected from the group consisting of an active pharmaceutical ingredient, an active nutraceutical ingredient, and an active cosmeceutical ingredient.

23. The process of claim 11, wherein a dry substance of the aqueous dispersion consists of the (meth)acrylate copolymer (a) and the dispersing agent (b).

24. The process of claim 11, wherein a solid content of the aqueous dispersion is 10 to 50% by weight, based on a total weight of the aqueous dispersion, and a water content is 90 to 50% by weight, based on the total weight of the dispersion.

25. The process of claim 11, wherein a solid content of the aqueous dispersion is 15 to 30% by weight, based on a total weight of the aqueous dispersion, and a water content is 85 to 70% by weight, based on the total weight of the aqueous dispersion.

26. The process of claim 11, wherein the (meth)acrylate copolymer (a) of the ready to use composition comprises 50 to 70% by weight of methyl methacrylate, 20 to 40% by weight of ethyl acrylate and 2 to 12% by weight of 2-trimethylammoniumethyl methacrylate chloride.

27. The process of claim 11, which occurs at a temperature of less than 35° C.

28. The process of claim 11, which occurs at a temperature of 15 to 25° C.

* * * * *